United States Patent
Lin

(10) Patent No.: US 8,908,170 B2
(45) Date of Patent: Dec. 9, 2014

(54) METHOD FOR DETECTING DEFECT OF DISPLAY PANEL AND RELATED DETECTING DEVICE

(71) Applicant: Shenzhen China Star Optoelectronics Technology Co., Ltd., Shenzhen, Guangdong (CN)

(72) Inventor: Yung-Yu Lin, Shenzhen (CN)

(73) Assignee: Shenzhen China Star Optoelectronics Technology Co., Ltd., Shenzhen, Guangdong (CN)

(*) Notice: Subject to any disclaimer, the term of this patent is extended or adjusted under 35 U.S.C. 154(b) by 13 days.

(21) Appl. No.: 13/809,007

(22) PCT Filed: Jan. 4, 2013

(86) PCT No.: PCT/CN2013/070005
§ 371 (c)(1),
(2), (4) Date: Jan. 8, 2013

(87) PCT Pub. No.: WO2014/101304
PCT Pub. Date: Jul. 3, 2014

(65) Prior Publication Data
US 2014/0185048 A1 Jul. 3, 2014

(30) Foreign Application Priority Data
Dec. 27, 2012 (CN) .......................... 2012 1 0580603

(51) Int. Cl.
*G01N 21/00* (2006.01)
*G06K 9/00* (2006.01)
*G01N 21/88* (2006.01)

(52) U.S. Cl.
CPC ................................ *G01N 21/8806* (2013.01)
USPC .......................... 356/237.1; 349/192; 382/145

(58) Field of Classification Search
CPC .. G02F 1/1309; G09G 3/006; G09G 2330/10; G09G 2320/029; G01N 2021/9513; G01N 21/8803; G01N 21/95; G06T 7/0004
USPC ..................... 356/237.1–237.5, 239.1, 239.2; 349/192, 8, 54; 345/87, 214; 348/191, 348/180, 615, 743; 382/131, 141, 149; 324/770
See application file for complete search history.

(56) References Cited

U.S. PATENT DOCUMENTS

| 6,359,662 B1 * | 3/2002 | Walker ........................ 348/743 |
| 6,714,670 B1 * | 3/2004 | Goldsworthy et al. ....... 382/149 |
| 6,791,682 B2 * | 9/2004 | Kobayashi ................ 356/239.1 |
| 7,301,523 B2 * | 11/2007 | Kamei ........................ 345/102 |
| 8,570,506 B2 * | 10/2013 | Li et al. ..................... 356/237.2 |
| 2006/0176935 A1 * | 8/2006 | Hiroki .......................... 375/132 |

(Continued)

FOREIGN PATENT DOCUMENTS

JP 06-236162 * 8/1994
JP 2005338261 A * 12/2005

*Primary Examiner* — Hoa Pham
(74) *Attorney, Agent, or Firm* — Andrew C. Cheng

(57) ABSTRACT

The present invention provides a method for detecting a defect of a display panel and related defect detecting device. The method includes: utilizing lights having different colors to illuminate the display panel; obtaining a plurality of corresponding grey-scale diagrams when the lights illuminate the display panel; and determining whether the display panel has a defect. If the grey-scale diagrams indicate a grey-scale difference, determining that the display panel has a defect. In this way, the present invention is able to raise defect detecting ability for the display panel and prevent from missing the defects.

13 Claims, 8 Drawing Sheets

(56) References Cited

U.S. PATENT DOCUMENTS

| | | | |
|---|---|---|---|
| 2006/0215898 A1* | 9/2006 | Song et al. | 382/141 |
| 2006/0222232 A1* | 10/2006 | Ishikawa | 382/141 |
| 2008/0111805 A1* | 5/2008 | Chang | 345/208 |
| 2010/0156778 A1* | 6/2010 | Yamagishi | 345/102 |
| 2011/0080534 A1* | 4/2011 | Perng et al. | 349/9 |

* cited by examiner

METHOD FOR DETECTING DEFECT OF DISPLAY PANEL AND RELATED DETECTING DEVICE

BACKGROUND OF THE INVENTION

1. Field of the Invention

The invention relates to a detecting method for a display panel, and more particularly, to a method for detecting a defect of a display panel and related detecting device.

2. Description of the Prior Art

As time goes by, LCD display capable of displaying high-quality images become more and more popular. However, according to current manufacturing techniques, it's hard to totally prevent display defects. Therefore, it's essential to detect the defects of the LCD panel in the manufacturing process.

In the current techniques, a white light is often used to illuminate the display panel and a corresponding grey-scale diagram is obtained. And then, whether or not a grey scale difference occurs can be determined according to the grey-scale diagram and this information can be used to determine whether there is a defect on the display panel. However, some defects do not introduce an apparent grey-scale difference when the white light is used to illuminate the display panel. This means the grey-scale difference is not easy to distinguish. Therefore, this defect detecting method may miss some defects and its capability of detecting defects of the display panel is not good.

From the above, it can be seen that it is necessary to provide a defect detecting method for display panel and related detecting device, in order to solve the above-mentioned problem.

SUMMARY OF THE INVENTION

It is therefore one of the primary objectives of the claimed invention to provide a defect detecting method for display panel and related detecting device to further raise the defect detecting ability for the display panel and prevent from missing defects.

According to an exemplary embodiment of the claimed invention, a method for detecting a defect of a display panel is disclosed. The defect detecting method comprises: utilizing a red light, a green light, and a blue light to illuminate the display panel; obtaining corresponding three pixel electrode diagrams when the red light, the green light, and the blue light illuminate the display panel; obtaining a first grey-scale diagram, a second grey-scale diagram, and a third grey-scale diagram when the red light, the green light, and the blue light illuminate the display panel according to the three pixel electrode diagrams; and determining whether the display panel has a defect; wherein if the first grey-scale diagram, the second grey-scale diagram, and the third grey-scale diagram indicate a grey-scale difference, determining that the display panel has a defect.

In one aspect of the present invention, the method further comprises: utilizing a white lights to illuminate the display panel; obtaining a fourth grey-scale diagram when the white light illuminate the display panel; and determining whether the display panel has a detect, according to the fourth grey-scale diagram If the fourth grey-scale diagram does not indicate a grey-scale difference, determining that the display panel does not have a defect and performing the step of utilizing lights having different colors to illuminate the display panel.

In another aspect of the present invention, if the fourth grey-scale diagram indicates a grey-scale difference, then determining that the display panel has a defect.

According to another exemplary embodiment of the claimed invention, a method for detecting a defect of a display panel is disclosed. The defect detecting method comprises: utilizing lights having different colors to illuminate the display panel; obtaining a plurality of corresponding grey-scale diagrams when the lights illuminate the display panel; and determining whether the display panel has a defect. If the grey-scale diagrams indicate a grey-scale difference, determining that the display panel has a defect.

In one aspect of the present invention, the step of obtaining the grey-scale diagrams when the lights illuminate the display panel comprises: obtaining corresponding pixel electrode diagrams through a shooting process when the lights illuminate the display panel; and obtaining the grey-scale diagrams according to the pixel electrode diagrams.

In another aspect of the present invention, the lights having different colors comprise a red light, a green light, a blue light, and a first grey-scale diagram, a second grey-scale diagram, and a third grey-scale diagram are obtained when the red light, the green light, and the blue light illuminate the display panel.

In still another aspect of the present invention, the method further comprises: utilizing a white lights to illuminate the display panel; obtaining a fourth grey-scale diagram when the white light illuminate the display panel; and determining whether the display panel has a defect according to the fourth grey-scale diagram. If the fourth grey-scale diagram does not indicate a grey-scale difference, determining that the display panel does not have a defect and performing the step of utilizing lights having different colors to illuminate the display panel.

In yet another aspect of the present invention, if the fourth grey-scale diagram indicates a grey-scale difference, then determining that the display panel has a defect.

According to another exemplary embodiment of the claimed invention, a detect detecting device for a display panel is disclosed. The defect detecting device comprises a light source module, for utilizing lights having, different colors to illuminate the display panel, an obtaining module, for obtaining a plurality of corresponding grey-scale diagrams when the light source module utilizes lights having different colors to illuminate the display panel, and to processing module for determining whether the display panel has a defect according to the grey-scale diagrams obtained by the obtaining module. If the grey-scale diagrams indicate a grey-scale difference, the processing module determines that the display panel has a detect.

In one aspect of the present invention, the defect detecting device further comprises a shooting module for shooting pixel electrode diagrams when the lights illuminate the display panel. The obtaining module obtains the grey-scale diagrams according to the pixel electrode diagrams obtained by the shooting module.

In another aspect of the present invention, the lights having different colors comprise a red light, a green light, a blue light. A first grey-scale diagram, a second grey-scale diagram, and a third grey-scale diagram are obtained when the red light, the green light, and the blue light illuminate the display panel, respectively.

In still another aspect of the present invention, the light source module for further utilizing a white light to illuminate the display panel. The shooting module shoots a pixel electrode diagram when the white light illuminates the display panel. The obtaining module obtains a fourth grey-scale diagram according to the pixel electrode diagram when the white light illuminates the display panel.

In yet another aspect of the present invention, the processing module determines whether the display panel has a defect further according to the fourth grey-scale diagram. If the fourth grey-scale diagram does not indicate a grey-scale difference, the processing module determines that the display panel does not have a defect. If the fourth grey-scale diagram indicates a grey-scale difference, the processing module determines that the display panel has a defect.

In contrast to the prior art, the present invention utilizes lights having different colors to illuminate the display panel, obtains corresponding grey-scale diagrams, and determines whether the display panel has a defect according to the grey-scale diagrams. Therefore, the present invention is able to raise the defect detecting ability for display panel and prevent from missing defects.

These and other objectives of the claimed invention will no doubt become obvious to those of ordinary skill in the art after reading the following detailed description of the preferred embodiment that is illustrated in the various figures and drawings.

DETAILED DESCRIPTION OF THE PREFERRED EMBODIMENT

The present invention provides A method for detecting a defect of a display panel and related defect detecting device. Specifically, the present invention defect detecting method utilizes lights having different colors to illuminate the display panel, obtains a plurality of corresponding grey-scale diagrams, and determining whether the display panel has a defect according to the grey scale difference indicated by the grey-scale diagrams. Please note, defects may include pixel dropping, uneven pixel distribution, water or ITO remains, and these defects all result in a grey-scale difference when lights having different color illuminate the display panel.

Figure 1:
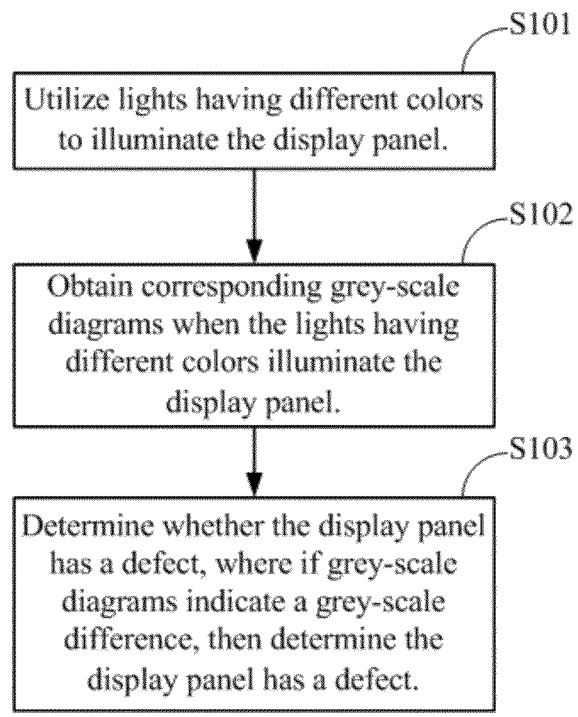
FIG. 1 is a flow chart illustrating a method of detecting a defect of as display panel according to an embodiment of the present invention.

Please refer to FIG. 1, which is a flow chart illustrating a method of defecting a defect of a display panel according to an embodiment of the present invention. The detect detecting method comprises following steps:

Step S101: utilize lights having different colors to illuminate the display panel.

Figure 2:
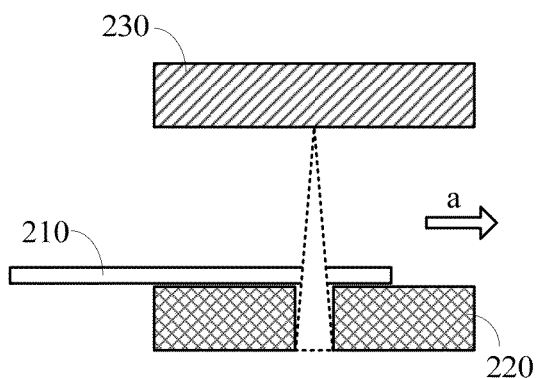
FIG. 2 is a diagram showing a first step of the defect detecting procedure according to an embodiment of the present invention.
Figure 3:
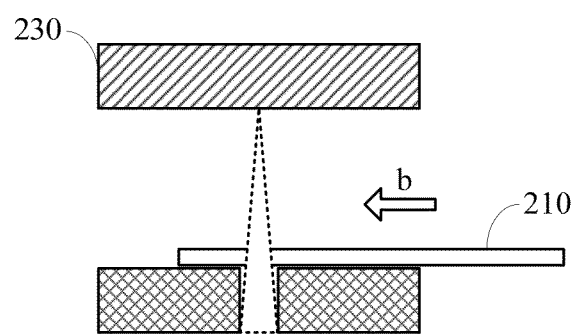
FIG. 3 is a diagram showing a second step of the defect detecting procedure according to an embodiment of the present invention.
Figure 4:
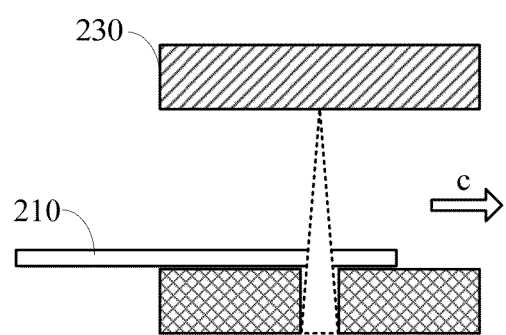
FIG. 4 is a diagram showing a third step of the defect detecting procedure according to an embodiment of the present invention.

Please refer to FIG. 2, FIG. 3, and FIG. 4. FIG. 2 is a diagram showing a first step of the detect detecting procedure according to an embodiment of the present invention. FIG. 3 is a diagram showing a second step of the defect detecting procedure according to an embodiment of the present invention. FIG. 4 is a diagram showing a third step of the defect detecting procedure according to an embodiment of the present invention. In this embodiment, the display panel 210 to be detected is uploaded on the detecting platform 220. The optical defect detecting machine 230 starts to generate lights having different color to illuminate the display panel 210.

In this embodiment, in order to reduce the cost and raise the defect detecting ability, optimally, the lights having different colors are preferably a red light, a green light, and a blue light. Please note, this is not a limitation of the present invention. In another embodiment, any two of the aforementioned lights can be selected or a light having another color can also be selected as long as there are two lights having different color being selected. Furthermore, the present invention does not limit the illuminating order of the above-mentioned lights. It means the order of utilizing these lights to illuminate the display panel can be changed by demands.

Step S102: obtain a plurality of corresponding grey-scale diagrams when the lights having different colors illuminate the display panel.

Figure 5:
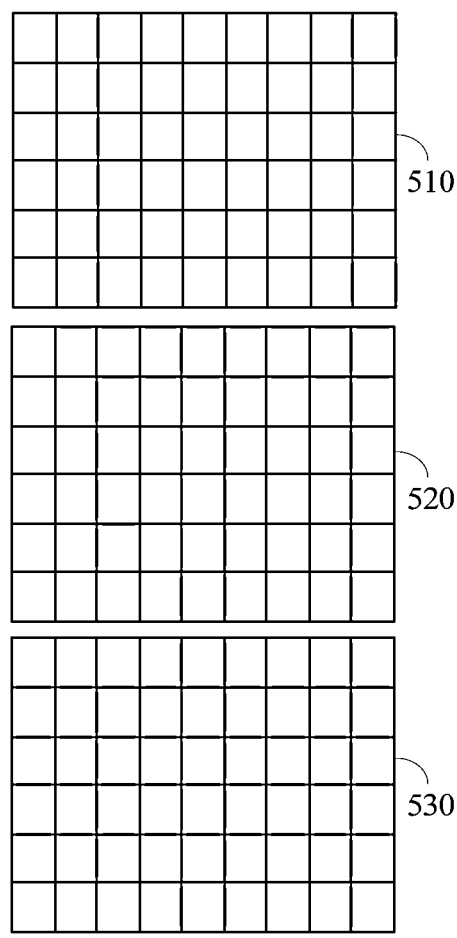
FIG. 5 is a grey-scale diagram showing that the gray-scale is normal when a red light, a green light, and a blue light illuminate the display panel.

Please refer to FIG. 2 in conjunction with FIG. 5. FIG. 5 is a grey-scale diagram showing that the gray-scale is normal when a red light, a green light, and a blue light illuminate the display panel. The optical defect detecting machine 230 generates a red light to illuminate the display panel 210, and then the examiner or a transferring device moves the display panel 210 along the arrow direction "a" in a speed complied with the defection demand.

When the display panel 210 moves, the shouting device (not shown) set up on the detecting platform 220, such as a CCD camera, shoots a first corresponding, pixel electrode diagram when the display panel 210 is illuminated by a red light and obtains a first grey-scale diagram 510 corresponding to the first pixel electrode diagram.

Please refer to FIG. 3 in conjunction with FIG. 5. After obtaining the first grey-scale diagram 510, the optical defect detecting machine 230 generates a green light to illuminate the display panel 210, and then the examiner or a transferring device moves the display panel 210 along the reversed direction "b". Simultaneously, the shooting device shoots a second corresponding pixel electrode diagram when the display panel 210 is illuminated by a green light and obtains a second grey-scale diagram 520 corresponding to the second pixel electrode diagram.

Please refer to FIG. 4 in conjunction with FIG. 5. After obtaining the second grey-scale diagram 520, the optical detect detecting machine 230 generates a blue light to illuminate the display panel 210, and then the examiner or a transferring device moves the display panel 210 along the direction "c". Simultaneously, the shooting device shoots a third corresponding pixel electrode diagram when the display panel 210 is illuminated by a blue light and obtains a third grey-scale diagram 530 corresponding to the second pixel electrode diagram.

Please note, in another embodiment of the present invention, the first pixel electrode diagram, the second pixel electrode diagram, and the third pixel electrode diagram can be obtained first, and then the first grey-scale diagram 510, the second grey-scale diagram 520, and the third grey-scale diagram 530 can be correspondingly obtained later. In addition, the procedure and basic theory of obtaining the grey-scale diagrams from the pixel electrode diagrams have been known by one having average skills in the art, and thus omitted here.

Moreover, the above-mentioned order of utilizing the red light, the green light, and the blue light is not a limitation of the present invention. It can be changed, and all these changes all obey the spirit of the present invention.

Step S103: determine whether the display panel has a defect, where if grey-scale diagrams indicate a grey-scale difference, then determine the display panel has a defect.

Figure 6:
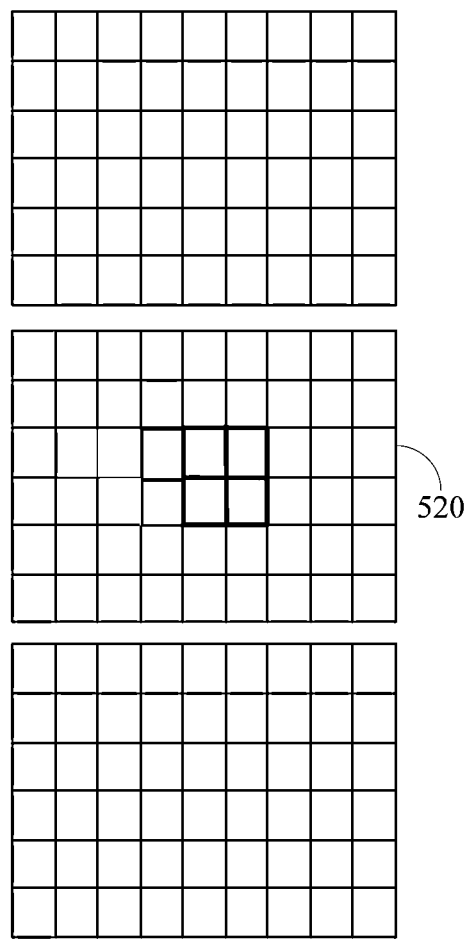
FIG. 6 is a grey-scale diagram showing that the gray-scale is abnormal when a red light, a green light, and a blue light illuminate the display panel.

In this embodiment, if at least one of the first grey-scale diagram 510, the second grey-scale diagram 520, and the third grey-scale diagram 530 indicates a grey-scale difference. For example, please refer to FIG. 6, the second grey-scale diagram 520 has a grey-scale difference, then the display panel 210 is determined to have a defect. Furthermore, according to the actual condition of the grey-scale difference, the defect can be identified as a water remains or another kind of defect. On the other hand, if all of the first grey-scale diagram 510, the second grey-scale diagram 520, and the third grey-scale diagram 530 do not indicate a grey-scale difference, then the display panel 210 is determined to have no defects.

To sum up, in the above embodiment, the present invention utilizes the red light, the green light, and the blue light to illuminate the display panel, obtains corresponding the first grey-scale diagram 510, the second grey-scale diagram 520, and the third grey-scale diagram 530, and determines whether the display panel has a defect according to whether the grey-scale difference occurred on the first grey-scale diagram 510, the second grey-scale diagram 520, and the third grey-scale diagram 530. Therefore, the present invention can raise the detecting ability of the optical defect detecting machine and prevent from missing defects.

Figure 7:
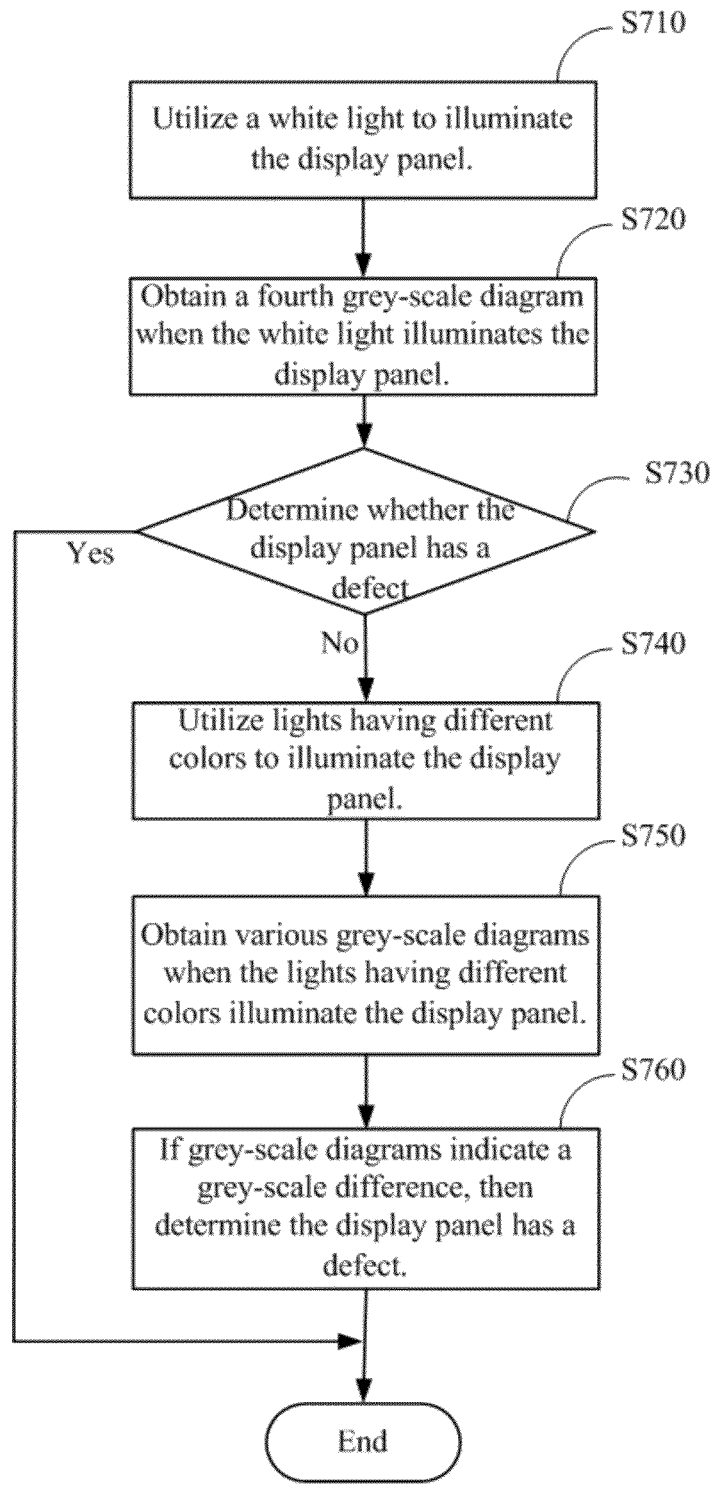
FIG. 7 is a flow chart illustrating a method of detecting a defect of a display panel according to another embodiment of the present invention.

Please refer to FIG. 7 showing a flow chart illustrating a method of detecting a defect of a display panel according to another embodiment of the present invention. In this embodiment, the difference between this embodiment and the above-mentioned embodiment is that a white light is firstly used to detect the defects. Specifically, this detecting, procedure in this embodiment comprises following steps:

Step 710: utilize a white light to illuminate the display panel.

Step 720: obtain a fourth grey-scale diagram when the white light illuminates the display panel.

Step 730: determine whether the display panel has a defect according to the fourth grey-scale diagram. If the fourth grey-scale diagram indicates a grey scale difference, then determine that the display panel has a defect without performing the following steps of utilizing other lights having different color to perform the detect detection.

Step S740: utilize lights having different colors to illuminate the display panel.

Step S750: obtain a plurality of corresponding grey-scale diagrams when the lights having different colors illuminate the display panel.

Step S760: determine whether the display panel has a defect, where if grey-scale diagrams indicate a grey-scale difference, then determine the display panel has as defect.

Figure 8:
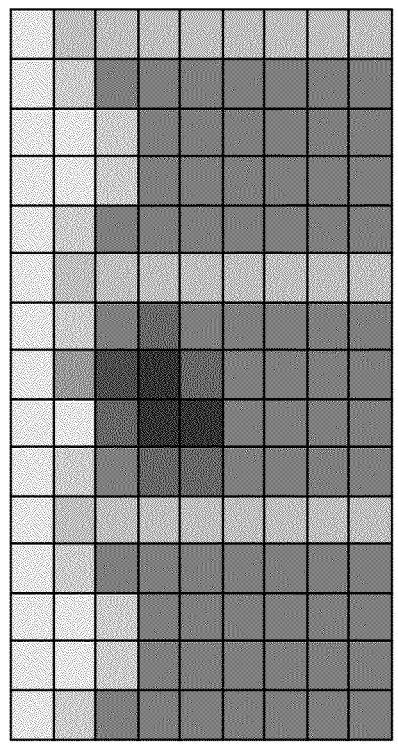
FIG. 8 is a grey-scale diagram showing that the gray-scale is abnormal when a white light illuminates the display panel.

In this embodiment, the white light is firstly used to illuminate the display panel, and then the red light, green light, and blue light are utilized to illuminate the display panel. The main reason is: the grey-scale diagram corresponding to the white light, as shown in FIG. 8, can be used to detect some common defects such as pixel drops or uneven pixel distribution. Therefore, the white light can be used firstly, and then the lights having different colors can be used later to detect some special defects such as water or ITO remains.

Please note, in this embodiment, the present invention firstly use the white light to perform the defect detection and then use the red light, green light, and blue light to perform the defect detection. This can also raise the defect detecting ability of the optical defect detecting machine and prevent from missing defects.

Figure 9:
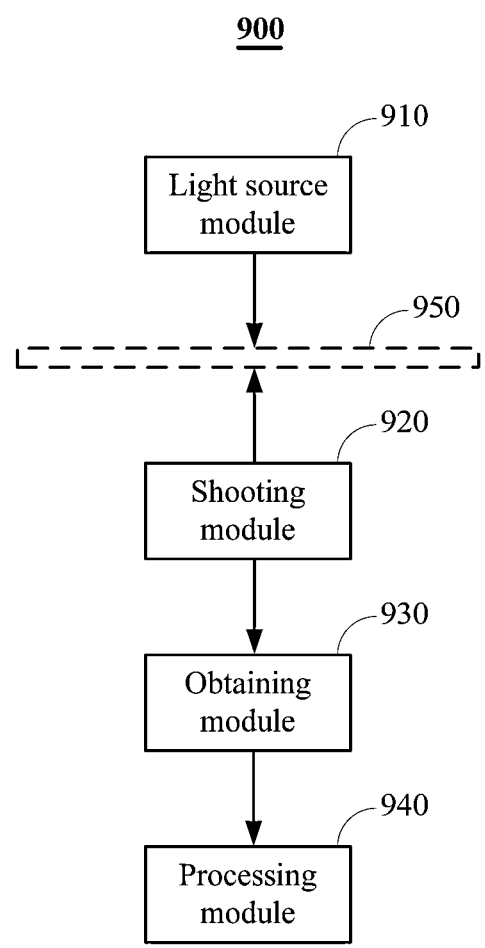
FIG. 9 is a diagram showing a defect detecting device according to an embodiment of the present invention.

Please refer to FIG. 9, which is a diagram showing a defect detecting device according to an embodiment of the present invention. In this embodiment, the defect detecting device 900 comprises a light source module 910, a shooting module 920, an obtaining module 930, and a processing module 940.

In this embodiment, the light module 910 can utilize lights having different colors to illuminate the display panel 950. As mentioned previously, the lights are preferably red light, green light, and blue light.

The shooting module is used to shoot the pixel electrode diagrams when the display panel 950 is respectively illuminated by the red light, green light, and blue light.

The obtaining module 930 is used to obtain the first grey-scale diagram, the second grey-scale diagram, and the third grey-scale diagram according to the pixel electrode diagrams obtained by the shooting module 920.

The processing module 940 is used to determine whether the display panel 950 has a defect according to the first grey-scale diagram, the second grey-scale diagram, and the third grey-scale diagram. If one of the first grey-scale diagram, the second grey-scale diagram, and the third grey-scale diagram indicates a grey-scale difference, then the processing module 940 determines that the display panel 950 has a defect.

In addition, in another embodiment, the source module 910 can firstly utilize a white light to illuminate the display panel 950, the shooting module 920 obtains a pixel electrode diagram when the white light illuminates the display panel 950, the obtaining module 930 obtains a fourth grey-scale diagram according to the pixel electrode diagram corresponding to the white light, and the processing module 940 determines whether the display panel 950 has a defect according to the fourth grey-scale diagram. In this embodiment, if the fourth grey-scale diagram does not indicate the grey scale difference, the processing module 940 determines that the display panel 950 does not have defects and then other lights having different colors are used to do further defect detections. On the other hand, if the fourth grey-scale diagram indicates a grey-scale difference, then the processing module 940 determines that the display module 950 has a defect, and other lights having different colors are no longer needed for further defect detections.

From the above, it can be seen that the present invention utilizes lights having different colors to illuminate the display panel, obtains corresponding grey-scale diagrams, and determines whether the display panel has a defect according to these grey-scale diagrams. Therefore, the present invention can raise the detecting ability of the optical defect detecting machine and prevent from missing defects.

Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A method for detecting a defect of a display panel, the method comprising:
utilizing a red light, a green light, and a blue light to illuminate the display panel;
obtaining corresponding three pixel electrode diagrams when the red light, the green light, and the blue light illuminate the display panel;
obtaining a first grey-scale diagram, a second grey-scale diagram, and a third grey-scale diagram when the red light, the green light, and the blue light illuminate the display panel according to the three pixel electrode diagrams; and
determining whether the display panel has a defect;
wherein if the first grey-scale diagram, the second grey-scale diagram, and the third grey-scale diagram indicate a grey-scale difference, determining that the display panel has a defect.

2. The method of claim 1, further comprising:
utilizing a white lights to illuminate the display panel;
obtaining a fourth grey-scale diagram when the white light illuminate the display panel; and
determining whether the display panel has a defect according to the fourth grey-scale diagram;
wherein if the fourth grey-scale diagram does not indicate a grey-scale difference, determining that the display panel does not have a defect and performing the step of utilizing lights having different colors to illuminate the display panel.

3. The method of claim 2, wherein if the fourth grey-scale diagram indicates a grey-scale difference, then determining that the display panel has a defect.

4. A method for detecting a defect of a display panel, the defect detecting method comprising:
utilizing lights having different colors to illuminate the display panel;
obtaining a plurality of corresponding grey-scale diagrams when the lights illuminate the display panel; and
determining whether the display panel has a defect;
wherein if the grey-scale diagrams indicate a grey-scale difference, determining that the display panel has a defect.

5. The method of claim 4, wherein the step of obtaining the grey-scale diagrams when the lights illuminate the display panel comprises:
obtaining corresponding pixel electrode diagrams through a shooting process when the lights illuminate the display panel; and
obtaining the grey-scale diagrams according to the pixel electrode diagrams.

6. The method of claim 4, wherein the lights having different colors comprise a red light, a green light, a blue light, and a first grey-scale diagram, a second grey-scale diagram, and a third grey-scale diagram are obtained when the red light, the green light, and the blue light illuminate the display panel.

7. The method of claim 6, further comprising:
utilizing a white lights to illuminate the display panel;
obtaining a fourth grey-scale diagram when the white light illuminate the display panel; and
determining whether the display panel has a defect according to the fourth grey-scale diagram;
wherein if the fourth grey-scale diagram does not indicate a grey-scale difference, determining that the display panel does not have a defect and performing the step of utilizing lights having different colors to illuminate the display panel.

8. The method of claim 7, wherein if the fourth grey-scale diagram indicates a grey-scale difference, then determining that the display panel has a defect.

9. A detecting device for defecting defect of a display panel, the defect detecting device comprising:
a light source module, for utilizing lights having different colors to illuminate the display panel;
an obtaining module, for obtaining a plurality of corresponding grey-scale diagrams when the light source module utilizes lights having different colors to illuminate the display panel; and
a processing module, for determining whether the display panel has a defect according to the grey-scale diagrams obtained by the obtaining module;
wherein if the grey-scale diagrams indicate a grey-scale difference, the processing module determines that the display panel has a defect.

10. The defect detecting device of claim 9, further comprising:
a shooting module, for shooting pixel electrode diagrams when the lights illuminate the display panel;
wherein the obtaining module obtains the grey-scale diagrams according to the pixel electrode diagrams obtained by the shooting module.

11. The defect detecting device of claim 9, wherein the lights having different colors comprise a red light, a green light, a blue light, and a first grey-scale diagram, a second grey-scale diagram, and a third grey-scale diagram are obtained when the red light, the green light, and the blue light illuminate the display panel, respectively.

12. The defect detecting device of claim 11, wherein the light source module for further utilizing a white light to illuminate the display panel, the shooting module shoots a pixel electrode diagram when the white light illuminates the display panel, and the obtaining module obtains a fourth grey-scale diagram according to the pixel electrode diagram when the white light illuminates the display panel.

13. The defect detecting device of claim 12, wherein the processing module determines whether the display panel has a defect further according to the fourth grey-scale diagram, wherein if the fourth grey-scale diagram does not indicate a grey-scale difference, the processing module determines that the display panel does not have a defect, and wherein if the fourth grey-scale diagram indicates a grey-scale difference, the processing module determines that the display panel has a defect.

* * * * *